United States Patent
Suryavanshi et al.

(10) Patent No.: US 9,758,476 B2
(45) Date of Patent: Sep. 12, 2017

(54) ORTHO-ALKYNYL ANILINES AND PROCESS FOR PREPARATION THEREOF

(71) Applicant: COUNCIL OF SCIENTIFIC & INDUSTRIAL RESEARCH, New Delhi (IN)

(72) Inventors: Gurunath Mallappa Suryavanshi, Maharashtra (IN); Anil Maruti Shelke, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/321,329

(22) PCT Filed: Jun. 22, 2015

(86) PCT No.: PCT/IN2015/000256
§ 371 (c)(1),
(2) Date: Dec. 22, 2016

(87) PCT Pub. No.: WO2015/198343
PCT Pub. Date: Dec. 30, 2015

(65) Prior Publication Data
US 2017/0197911 A1    Jul. 13, 2017

(30) Foreign Application Priority Data
Jun. 25, 2014    (IN) ............ 1701/DEL/2014

(51) Int. Cl.
*C07C 281/02*    (2006.01)
*C07D 317/66*    (2006.01)

(52) U.S. Cl.
CPC .......... *C07C 281/02* (2013.01); *C07D 317/66* (2013.01)

(58) Field of Classification Search
None
See application file for complete search history.

(56) References Cited

U.S. PATENT DOCUMENTS

| 4,864,032 A | 9/1989 | Demers |
| 6,093,843 A | 7/2000 | Chee et al. |

FOREIGN PATENT DOCUMENTS

WO    WO 2004-093544 A1    11/2004

OTHER PUBLICATIONS

International Search Report (ISR) for PCT/IN2015/000256; I.A. fd: Jun. 22, 2015, mailed Oct. 29, 2015, European Patent Office, Rijswijk, Netherlands.
International Preliminary Report on Patentability (IPRP) including the Written Opinion of the International Searching Authority (PCT Rule 44bis) for PCT/IN2015/000256; I.A. fd: Jun. 22, 2015, issued Dec. 27, 2016, by the International Bureau of WIPO, Geneva, Switzerland.
Zhang, L et al., "Multicomponent multicatalyst reactions $(MC)^2R$: one-pot synthesis of 3,4-dihydroquinolinones," Org Lett. May 3, 2013;15(9):2128-31. doi: 10.1021/ol4006008. Epub Apr. 19, 2013, Am. Chem. Soc., Washington, DC.

*Primary Examiner* — Kamal Saeed
(74) *Attorney, Agent, or Firm* — Sterne, Kessler, Goldstein & Fox P.L.L.C.

(57) ABSTRACT

The present invention relates to novel ortho alkynyl anilines of formula (I) which are useful in synthesis of drug intermediates and natural products and process for preparation of these ortho alkynyl anilines of formula (I) via copper catalyzed Multi Component Reactions (MCR).

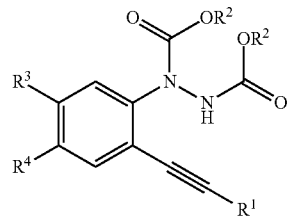

8 Claims, 1 Drawing Sheet

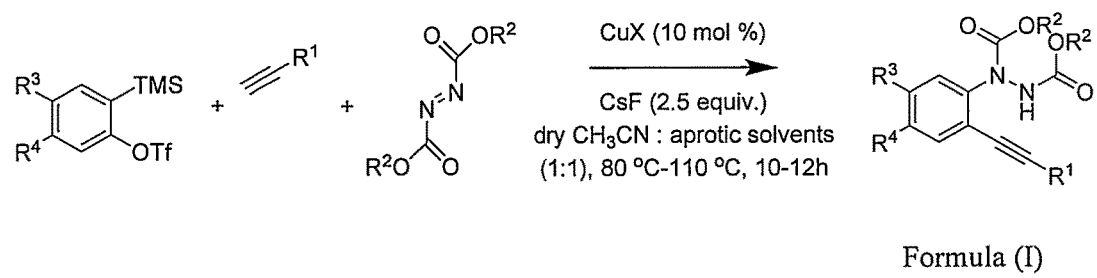
Formula (I)
FIG. 1: Scheme: 1
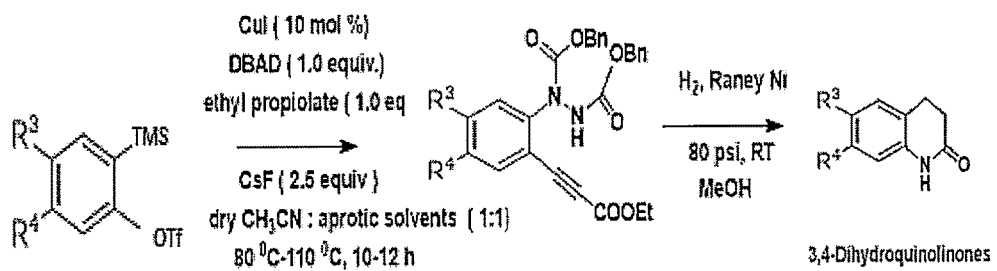
3,4-Dihydroquinolinones
FIG. 2: Scheme 2

ORTHO-ALKYNYL ANILINES AND PROCESS FOR PREPARATION THEREOF

FIELD OF THE INVENTION

The present invention relates to ortho alkynyl anilines of formula (I). Particularly, present invention relates to a one pot process for preparation of ortho alkynyl anilines of formula (I) via copper catalyzed Multi Component Reactions (MCR). More particularly, present invention relates to ortho alkynyl anilines of formula (I) useful in synthesis of drug intermediates and natural products.

BACKGROUND OF THE INVENTION

Multicomponent Reactions (MCRs) are one-pot reactions, in which three or more starting materials react to form a product, where basically all or most of the atoms contribute to the newly formed product. Speed, diversity, efficiency, atom-economy and environmental friendliness are some of the notable features of this class of reactions. The most important MCRs are the isocyanide-based reactions such as the Passerini three-component reaction and the Ugi four-component reaction. Moreover, a variety of heterocycles can be constructed using the MCR strategy, where zwitterionic intermediates are generated by the addition of nucleophile to activated C—C multiple bonds followed by their interception with a third component.

Arynes are highly electrophilic reactive intermediates, which have been extensively utilized in various carbon-carbon and carbon-heteroatom bond-forming reactions. One of the important aspects of aryne chemistry is multicomponent reaction, which mainly include the initial addition of nucleophiles to arynes and subsequent trapping of the aryl anion intermediate with electrophiles. If the nucleophile and electrophile do not belong to the same molecule, the overall process is a unique three-component coupling, where the aryne is inserted between the other two coupling partners (cqn (1)). This versatile transition-metal-free methodology has been applied to the synthesis of valuable heterocycles and in natural product synthesis. Ortho alkynyl anilines are the important precursor for the synthesis of substituted indoles, 3,4-hydroquinolinones & other heterocycles which are useful scaffold for synthesis of various drugs molecules and natural products.

Article titled, "Multicomponent Multicatalyst Reactions (MCR): One-Pot Synthesis of 3,4-Dihydroquinolinones" by Lei Zhang et al. published in *Org. Lett.*, 2013, 15 (9), pp 2128-2131 relates to a Rh/Pd/Cu catalyst system for synthesis of dihydroquinolinones in one-pot, two operations.

The reaction features the first triple metal-catalyzed transformations in one reaction vessel, without any intermediate workup.

Article titled, "Synthesis of 3-Sulfenyl- and 3-Selenylindoles by the Pd/Cu-Catalyzed Coupling of N,N-Dialkyl-2-iodoanilines and Terminal Alkynes, Followed by n-Bu₄NI-Induced Electrophilic Cyclization" by Yu Chen et al. published in *J. Org. Chem.*, 2009, 74 (17), pp 6802-6811 reports 3-Sulfenyl- and 3-selenylindoles that are readily synthesized by a two-step process involving the Pd/Cu-catalyzed crossing coupling of N,N-dialkyl-ortho-iodoanilines and terminal alkynes and subsequent electrophilic cyclization of the resulting N,N-dialkyl-ortho-(1-alkynyl) anilines with aryl sulfenyl chlorides or aryl selenyl chlorides. A variety of 3-sulfenyl- and 3-selenylindole derivatives bearing alkyl, vinylic, aryl, and heteroaryl substituents are prepared. The article further discloses preparation of 3-sulfonyl- and 3-sulfinylindoles by facile oxidation of the corresponding 3-sulfenylindoles.

Scheme: A

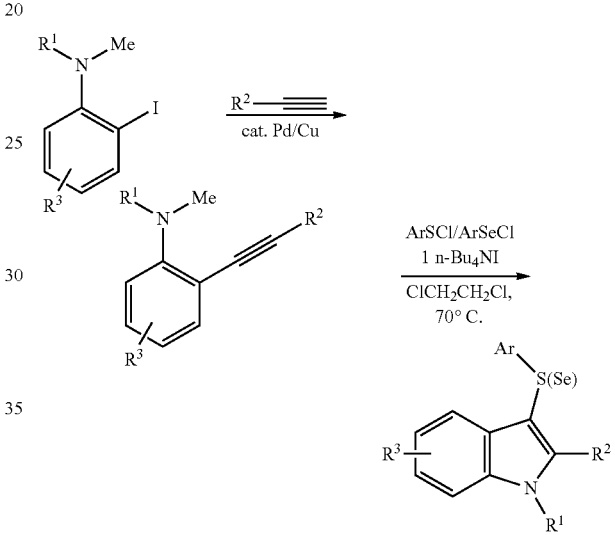

Article titled, "An Efficient, Microwave-Assisted, One-Pot Synthesis of Indoles under Sonogashira Conditions" by Chen Y et al. published in *Tetrahedron*, 2009; 65 (44); pp 8908-8915 reports an microwave-assisted, one-pot, three-component coupling reaction for the synthesis of indoles. The reaction is carried out in two steps under standard Sonogashira coupling conditions from an N-substituted/N,N-disubstituted 2-iodoaniline and a terminal alkyne, followed by the addition of acetonitrile and an aryl iodide.

Scheme: B

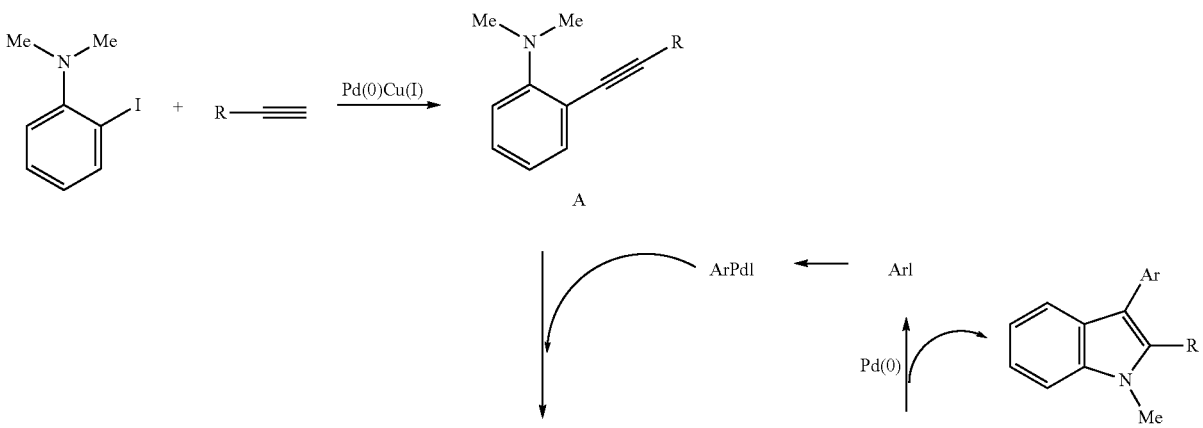

-continued

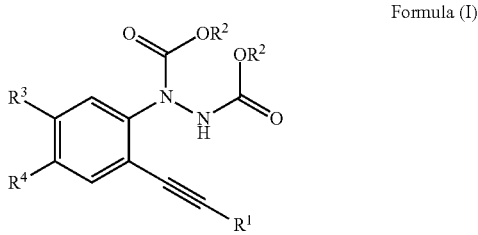

Article titled "Copper-catalyzed arylation of alkenyl aziridines via three-component coupling reaction involving alkynes and benzyne" by F Berti et al. published in *Synlett*, 2012; 23(17); pp 2463 reports alkenyl aziridines which can be successfully arylated in a three-component coupling triggered by in situ generated benzyne with a simple copper catalyst (CuI-PPh$_3$), without the need of any palladium salts. A new domino reaction with ethyl propionate to give tetrahydrophenanthridine is also described.

The processes described in the art involves activated systems which are air and moisture sensitive, are multiple step processes and involve use of expensive catalyst thereby making the process costly and industrially not feasible. In view of the above, there remains a need in the art to provide a process for synthesis of ortho alkynyl anilines that ameliorates the drawback of the known processes, which remains the objective of the invention.

OBJECTIVES OF INVENTION

The main objective of present invention is to provide an ortho alkynyl anilines of formula (I)

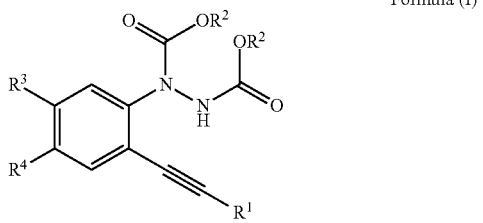

Formula (I)

Wherein,
R$^1$ is selected from substituted or unsubstituted alkyl, substituted or unsubstituted aryl, and ester;
R$^2$ is selected from substituted or unsubstituted alkyl (C$_1$ to C$_7$), substituted or unsubstituted aryl.
R$^3$ is selected from hydrogen, substituted or unsubstituted alkyl (C$_1$ to C$_7$), substituted or unsubstituted aryl, alkoxy.
R$^4$ is selected from hydrogen, substituted or unsubstituted alkyl(C$_1$ to C$_7$), substituted or unsubstituted aryl, alkoxy.
R3 and R4 jointly represent 1,3-dioxolyl.

Another objective of present invention is to provide a one-pot process for the preparation of protected ortho alkynyl anilines via multi component reaction of arynes.

Yet another object of the present invention is to provide ortho alkynyl anilines of formula (I) useful in synthesis of drug intermediates and natural products.

SUMMARY OF THE INVENTION

Accordingly, present invention provides a compound of formula (I)

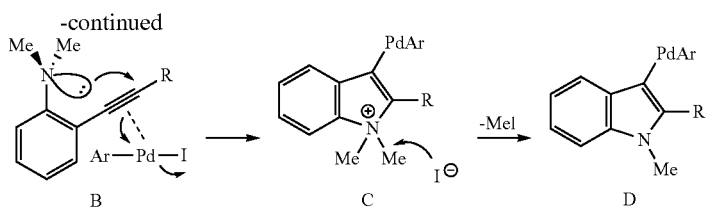

Formula (I)

R$^1$ is selected from substituted or unsubstituted alkyl, substituted or unsubstituted aryl, and ester;
R$^2$ is selected from substituted or unsubstituted alkyl(C$_1$ to C$_7$), substituted or unsubstituted aryl.
R$^3$ is selected from hydrogen, substituted or unsubstituted alkyl (C$_1$ to C$_7$), substituted or unsubstituted aryl, alkoxy.
R$^4$ is selected from hydrogen, substituted or unsubstituted alkyl(C$_1$ to C$_7$), substituted or unsubstituted aryl, alkoxy.
R3 and R4 jointly represent 1,3-dioxolyl.

In an embodiment of the present invention, said compounds of formula (I) are selected from the group consisting of:
i. dibenzyl1-(2-(3-ethoxy-3-oxoprop-1-yn-1-yl)phenyl)hydrazine-1,2-dicarboxylate;
ii. dibenzyl1-(2-(3-ethoxy-3-oxoprop-1-yn-1-yl)-4,5-dimethoxyphenyl)hydrazine-1,2-dicarboxylate,
iii. dibenzyl1-(6-(3-ethoxy-3-oxoprop-1-yn-1-yl)benzo[d][1,3]dioxol-5-yl)hydrazine-1,2-dicarboxylate and
iv. dibenzyl1-(2-(3-ethoxy-3-oxoprop-1-yn-1-yl)-4,5-dimethylphenyl) hydrazine-1,2-dicarboxylate.

In another embodiment, present invention provides a one-pot process for the preparation of compound of formula (I) comprising the steps of:
i. stirring the reaction mixture of (trimethylsilyl) aryl triflates with terminal alkyne and azodicarboxylate in presence of copper catalyst, cesium fluoride and solvent at temperature in the range of 80 to 110° C. for the period ranging from 8 to 15 h to obtain a mixture;
ii. Cooling the mixture as obtained in step (i) at room temperature in the range of 20 to 30° C. followed by filtering and purifying to obtain compound of formula 1.

In yet another embodiment of the present invention, stirring is carried out at temperature ranging from 80 to 110° C.

In yet another embodiment of the present invention, said copper catalyst used is copper (I) salt selected from the group consisting of copper chloride, copper bromide, copper iodide.

In yet another embodiment of the present invention, (trimethylsilyl) aryl triflates are selected from the group consisting of 2-(trimethylsilyl)phenyl trifluoromethanesulfonate, 4,5-dimethoxy-2-(trimethylsilyl)phenyl trifluoromethanesulfonate, 6-(trimethylsilyl)benzo[d][1,3]dioxol- 5-yl trifluoromethane-sulfonate, 4,5-dimethyl-2-(trimethylsilyl)phenyl trifluoromethanesulfonate.

In yet another embodiment of the present invention, terminal alkyne is selected from the group consisting of ethyl propiolate, methyl propiolate and butyl propiolate.

In yet another embodiment of the present invention, said azodicarboxylates are selected from dibenzyl azodicarboxylate and dialkyl azodicarboxylate.

In yet another embodiment of the present invention, said solvent is selected from the group consisting of dichloromethane, tetrahydrofuran, ethyl acetate, toluene, acetonitrile, dimethylformamide.

In yet another embodiment of the present invention, said compound is useful for synthesis of drug intermediates and natural product.

BRIEF DESCRIPTION OF THE DRAWINGS

FIG. 1: Scheme 1 represents steps for the preparation of compound of formula I.

FIG. 2: Scheme 2 represents synthesis of 3,4-dihydroquinolinones using o-alkynyl anilines of formula (I).

DETAILED DESCRIPTION OF THE INVENTION

The present invention provides a ortho-alkynyl anilines of formula (I) and a one-pot process for the preparation protected ortho-alkynyl anilines of formula (I) via multi component reaction of arynes.

Present invention provides a ortho alkynyl anilines of formula (I)

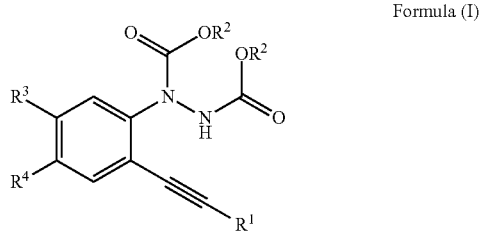

Formula (I)

Wherein
$R^1$ is selected from substituted or unsubstituted alkyl, substituted or unsubstituted aryl, and ester;
$R^2$ is selected from hydrogen, substituted or unsubstituted alkyl($C_1$ to $C_7$), substituted or unsubstituted aryl.
$R^3$ is selected from hydrogen, substituted or unsubstituted alkyl($C_1$ to $C_7$), substituted or unsubstituted aryl, alkoxy.
$R^4$ is selected from hydrogen, substituted or unsubstituted alkyl($C_1$ to $C_7$), substituted or unsubstituted aryl, alkoxy.
R3 and R4 jointly represent 1,3-dioxolyl.

The compounds of formula (I) are selected from the group consisting of dibenzyl 1-(2-(3-ethoxy-3-oxoprop-1-yn-1-yl)phenyl)hydrazine-1,2-dicarboxylate; dibenzyl 1-(2-(3-ethoxy-3-oxoprop-1-yn-1-yl)-4,5-dimethoxyphenyl)hydrazine-1,2-dicarboxylate, dibenzyl 1-(6-(3-ethoxy-3-oxoprop-1-yn-1-yl) benzo[d][1,3]dioxol-5-yl)hydrazine-1,2-dicarboxylate and dibenzyl 1-(2-(3-ethoxy-3-oxoprop-1-yn-1-yl)-4,5-dimethylphenyl) hydrazine-1,2-dicarboxylate.

The present invention provides a one-pot process for synthesis of compounds of formula (I), wherein said process comprises stirring the reaction mixture of (trimethylsilyl) aryl triflates with terminal alkyne and azodicarboxylate in presence of copper catalyst, cesium fluoride and suitable solvent at temperature ranging from 80-110° C. for the period ranging from 8 to 15 h to obtain the desired product of formula (I) with yield >80%. (Scheme 1).

(Trimethylsilyl) aryl triflates are selected from 2-(trimethylsilyl)phenyl trifluoromethanesulfonate, 4,5-dimethoxy-2-(trimethylsilyl)phenyl trifluoromethanesulfonate, 6-(trimethylsilyl)benzo[d][1,3]dioxol-5-yl trifluoromethanesulfonate, 4,5-dimethyl-2-(trimethylsilyl)phenyl trifluoromethanesulfonate and the like.

Terminal alkynes are selected from ethyl propiolate, methyl propiolate, butyl propiolate and the like.

Azodicarboxylates are selected from dibenzyl azodicarboxylate, dialkyl azodicarboxylate and the like.

Solvent used is selected from dichloromethane, tetrahydrofuran, ethyl acetate, toluene, acetonitrile, dimethylformamide and the like.

In the process, arynes are generated in situ from 2-(trimethylsilyl) aryl triflates and cesium fluoride. The temperature of the reaction is maintained in the range of 80-110° C.

The copper catalyst is selected from copper (I) salt such as copper halide, the solvent is selected from polar aprotic solvent such as DCM, THF, ethyl acetate, toluene, acetonitrile, DMF and the like.

These ortho-alkynyl anilines of formula (I) are useful as intermediates for synthesis of compounds that can be used for synthesis of indoles, quinolinones, in drug synthesis and natural products.

The present invention provides the use of o-alkynyl anilines of formula (I) for synthesis of 3,4-dihydroquinolinones (Scheme 2).

EXAMPLES

The compounds of formula (I) are also useful for synthesis of drug intermediates and natural products like cartiolol, aripiprazole and NMDA antagonist.

Following examples are given by way of illustration and therefore should not be construed to limit the scope of the invention.

General Experimental Procedure for Preparation of O-Alkynyl Anilines

Terminal alkynes (1.0 mmol), CuI (10-20 mg, 0.03 to 0.08 mmol) and CsF (0.365 g, 2.4 mmol) were charged to an oven-dried flask under the protection of nitrogen. Then the aryl triflates (1.2 mmol) were added by syringe with the mixture of $CH_3CN$ and aprotic solvents ranging from DCM, THF, ethyl acetate, toluene, acetonitrile, DMF and the like (3: 3 mL). The reaction mixture was stirred at 110° C. for 12 h and then cooled to room temperature 25° C. The suspension was filtered through a pad of cellite and the filtrate was concentrated under reduced pressure. The residue was purified by flash chromatography on a silica gel column to provide the desired product.

Example 1

Synthesis of Dibenzyl 1-(2-(3-ethoxy-3-oxoprop-1-yn-1-yl) phenyl) hydrazine-1,2-dicarboxylate

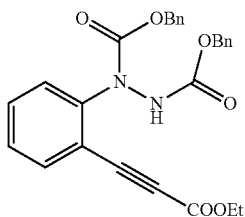 [SMILES: CCOC(=O)C#Cc1ccccc1N(NC(=O)OCc1ccccc1)C(=O)OCc1ccccc1]

Yield: 80%; colorless liquid $^1$H NMR (200 MHz, CDCl$_3$): δ 1.22-1.29 (t, J=7.0 Hz, 3H), 4.08-4.20 (q, J=7.0 Hz 2H), 5.10-5.27 (S, 4H). 7.0-7.4 (m, 14H); $^{13}$C NMR (50 MHz, CDCl$_3$): δ 14.2, 63.0, 67.2, 83.0, 89.1, 105.5, 113.0, 118.3, 127.0, 128.5, 132.1, 136.6, 146.8, 152.3, 155.5, 157.2

Example 2

Synthesis of Dibenzyl 1-(2-(3-ethoxy-3-oxoprop-1-yn-1-yl)-4,5-dimethoxyphenyl)hydrazine-1,2-dicarboxylate

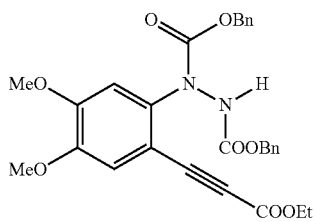

Yield: 85%; gummy liquid $^1$H NMR (200 MHz, CDCl$_3$): δ 1.24-1.28 (t, J=7.0 Hz, 3H), 3.9 (S, 6H), 4.10-4.24 (q, J=7.0 Hz 2H), 5.12-5.28 (S, 4H); $^{13}$C NMR (50 MHz, CDCl$_3$): δ 14, 58, 64, 68, 83, 88, 97, 100, 120, 128, 129, 137, 140, 150, 153, 156.

Example 3

Synthesis of dibenzyl 1-(6-(3-ethoxy-3-oxoprop-1-yn-1-yl) benzo[d][1,3]dioxol-5-yl)hydrazine-1,2-dicarboxylate

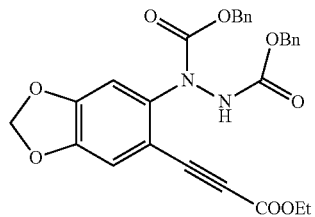 [SMILES: CCOC(=O)C#Cc1cc2c(cc1N(NC(=O)OCc1ccccc1)C(=O)OCc1ccccc1)OCO2]

Yield: 82%; colorless liquid $^1$H NMR (200 MHz, CDCl$_3$): δ 1.26 (t, J=7.1 Hz, 3H), 4.20 (q, J=7.1 Hz 2H), 5.21 (s, 4H), 6.02 (s, 2H) 6.82-7.43 (m, 12H); $^{13}$C NMR (50 MHz, CDCl$_3$): δ 14.4, 62.1, 66.5, 84.0, 92.3, 99.1, 120.2, 126.5, 127.3, 128.9, 134.5, 149.6, 150.1, 152.1, 156.4.

Example 4

Synthesis of dibenzyl 1-(2-(3-ethoxy-3-oxoprop-1-yn-1-yl)-4,5-dimethylphenyl)hydrazine-1,2-dicarboxylate

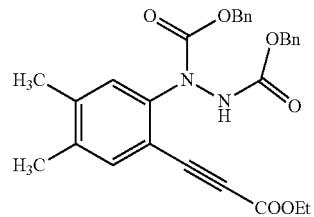 [SMILES: CCOC(=O)C#Cc1cc(C)c(C)cc1N(NC(=O)OCc1ccccc1)C(=O)OCc1ccccc1]

Yield: 78%; colorless liquid $^1$H NMR (200 MHz, CDCl$_3$): δ 1.27 (t, J=7.2 Hz, 3H), 2.21 (s, 3H), 2.30 (s, 3H), 4.1-4.3 (q, J=7.2 Hz, 2H), 5.2 (S, 4H). 6.9-7.5 (m, 12H); $^{13}$C NMR (50 MHz, CDCl$_3$): δ 13.2, 18.2, 18.8, 62.1, 66.7, 82.0, 90.0, 102.0, 111.0, 127.1, 127.6, 128.9, 133.7, 152.0, 156.0, 157.2.

ADVANTAGES OF INVENTION

1. No use of activated systems, one step and cheap process.
2. MCR helps to increase efficiency of synthetic organic routes to make a feasible process by reducing reaction time and their side products.
3. The ortho alkynyl anilines are the key intermediate for substituted indoles; 3, 4-hydroquinolinones which are useful scaffold for synthesis of various drugs and natural products and other heterocycles.

The invention claimed is:
1. A compound of formula (I)

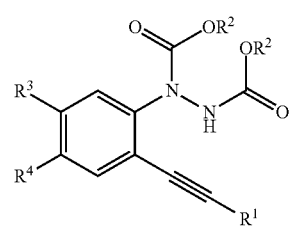

Formula (I)

wherein,
R$^1$ is selected from hydrogen, substituted or unsubstituted alkyl, substituted or unsubstituted aryl, and ester;
R$^2$ is selected from hydrogen, substituted or unsubstituted alkyl(C$_1$ to C$_7$), and substituted or unsubstituted aryl;
R$^3$ is selected from hydrogen, substituted or unsubstituted alkyl(C$_1$ to C$_7$), substituted or unsubstituted aryl, and alkoxy;
R$^4$ is selected from hydrogen, substituted or unsubstituted C$_1$ to C$_7$ alkyl, substituted or unsubstituted aryl, and alkoxy; and
R$^3$ and R$^4$ jointly represent 1,3-dioxolyl.

2. The compound as claimed in claim 1, wherein said compound of formula (I) are selected from the group consisting of:
  i. Dibenzyl1-(2-(3-ethoxy-3-oxoprop-1-yn-1-yl)phenyl) hydrazine-1,2-dicarboxylate;
  ii. Dibenzyl1-(2-(3-ethoxy-3-oxoprop-1-yn-1-yl)-4,5-dimethoxyphenyl)hydrazine-1,2-dicarboxylate,
  iii. Dibenzyl1-(6-(3-ethoxy-3-oxoprop-1-yn-1-yl)benzo[d][1,3]dioxol-5-yl)hydrazine-1,2-dicarboxylate and
  iv. Dibenzyl1-(2-(3-ethoxy-3-oxoprop-1-yn-1-yl)-4,5-dimethylphenyl) hydrazine-1,2-dicarboxylate.

3. A one-pot process for the preparation of a compound of formula (I) comprising the steps of:
  i. stirring a reaction mixture of (trimethylsilyl) aryl triflates with terminal alkyne and azodicarboxylate in the presence of a copper catalyst, cesium fluoride and solvent at a temperature in the range of 80 to 110° C. for a period ranging from 8 to 15 h to obtain a mixture;
  ii. cooling the mixture as obtained in step (i) at room temperature in the range of 20 to 30° C. followed by filtering and purifying to obtain compound of formula (I), wherein the compound of formula (I) is:

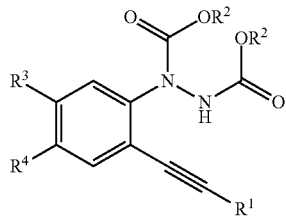

wherein,
  $R^1$ is selected from hydrogen, substituted or unsubstituted alkyl, substituted or unsubstituted aryl, and ester;
  $R^2$ is selected from hydrogen, substituted or unsubstituted alkyl($C_1$ to $C_7$), and substituted or unsubstituted aryl;
  $R^3$ is selected from hydrogen, substituted or unsubstituted alkyl($C_1$ to $C_7$), substituted or unsubstituted aryl, and alkoxy;
  $R^4$ is selected from hydrogen, substituted or unsubstituted $C_1$ to $C_7$ alkyl, substituted or unsubstituted aryl, and alkoxy; and
  $R^3$ and $R^4$ jointly represent 1,3-dioxolyl.

4. The process as claimed in claim 3, wherein said copper catalyst is a copper (I) salt selected from the group consisting of copper chloride, copper bromide, and copper iodide.

5. The process as claimed in claim 3, wherein the (trimethylsilyl) aryl triflates are selected from the group consisting of 2-(trimethylsilyl)phenyl trifluoromethanesulfonate, 4,5-dimethoxy-2-(trimethylsilyl)phenyl trifluoromethane-sulfonate, 6-(trimethylsilyl)benzo[d][1,3]dioxol-5-yl trifluoromethane-sulfonate, 4,5-dimethyl-2-(trimethylsilyl)phenyl trifluoromethanesulfonate.

6. The process as claimed in claim 3, wherein the terminal alkyne is selected from the group consisting of ethyl propiolate, methyl propiolate and butyl propiolate.

7. The process as claimed in claim 3, wherein said azodicarboxylate is selected from dibenzyl azodicarboxylate and dialkyl azodicarboxylate.

8. The process as claimed in claim 3, wherein said solvent is selected from the group consisting of dichloromethane, tetrahydrofuran, ethyl acetate, toluene, acetonitrile, and dimethylformamide.

* * * * *